US00PP26987P2

(12) United States Plant Patent
Dummen

(10) Patent No.: US PP26,987 P2
(45) Date of Patent: Jul. 26, 2016

(54) ***BIDENS* PLANT NAMED 'DUEBIGO14'**

(50) Latin Name: *Bidens ferulifolia*
Varietal Denomination: Duebigo14

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 156 days.

(21) Appl. No.: 14/120,876

(22) Filed: Jul. 7, 2014

(51) Int. Cl.
*A01H 5/02* (2006.01)

(52) U.S. Cl.
USPC ..... Plt./410

(58) Field of Classification Search
USPC ..... Plt./410
See application file for complete search history.

*Primary Examiner* — Keith Robinson
(74) *Attorney, Agent, or Firm* — C. A. Whealy

(57) ABSTRACT

A new and distinct cultivar of *Bidens* plant named 'Duebigo14', characterized by its compact, semi-upright to trailing and mounding plant habit; moderately vigorous growth habit; freely branching habit; freely flowering habit; large inflorescences with bright yellow orange-colored ray florets and dark yellow-colored disc florets; and strong peduncles that hold the inflorescences above and beyond the foliar plane.

1 Drawing Sheet

Botanical designation: *Bidens ferulifolia.*
Cultivar denomination: 'DUEBIGO14'.

BACKGROUND OF THE INVENTION

The present invention relates to a new and distinct cultivar of *Bidens* plant, botanically known as *Bidens ferulifolia* and hereinafter referred to by the name 'Duebigo14'.

The new *Bidens* plant is a product of a planned breeding program conducted by the Inventor in Rheinberg, Germany. The objective of the breeding program is to create compact *Bidens* plants with numerous large and attractive inflorescences.

The new *Bidens* plant originated from a cross-pollination made by the Inventor in Rheinberg, Germany in July, 2011 of a proprietary selection of *Bidens ferulifolia* identified as code number B08-1708-002, not patented, as the female, or seed, parent with a proprietary selection of *Bidens ferulifolia* identified as code number F-020-003, not patented, as the male, or pollen, parent. The new *Bidens* plant was discovered and selected by the Inventor as a single flowering plant from within the progeny of the stated cross-pollination in a controlled greenhouse environment in Rheinberg, Germany in May, 2013.

Asexual reproduction of the new *Bidens* plant by vegetative cuttings in a controlled environment in Rheinberg, Germany since June, 2013 has shown that the unique features of this new *Bidens* plant are stable and reproduced true to type in successive generations.

SUMMARY OF THE INVENTION

Plants of the new *Bidens* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Duebigo14'. These characteristics in combination distinguish 'Duebigo14' as a new and distinct *Bidens* plant:

1. Compact, semi-upright to trailing and mounding plant habit.
2. Moderately vigorous growth habit.
3. Freely branching habit.
4. Freely flowering habit.
5. Large inflorescences with bright yellow orange-colored ray florets and dark yellow-colored disc florets.
6. Strong peduncles that hold the inflorescences above and beyond the foliar plane.

Plants of the new *Bidens* differ primarily from plants of the female parent selection in plant habit as plants of the new *Bidens* are more compact than plants of the female parent selection.

Plants of the new *Bidens* differ primarily from plants of the male parent selection in growth habit as plants of the new *Bidens* are more vigorous than plants of the male parent selection.

Plants of the new *Bidens* can be compared to plants of *Bidens ferulifolia* 'Duebigon11', not patented. In side-by-side comparisons conducted in Rheinberg, Germany, plants of the new *Bidens* differed from plants of 'Duebigon11' in the following characteristics:

1. Plants of the new *Bidens* were more compact than plants of 'Duebigon11'.
2. Plants of the new *Bidens* had smaller leaves than plants of 'Duebigon11'.
3. Plants of the new *Bidens* had larger inflorescences than plants of 'Duebigon11'.
4. Plants of the new *Bidens* had darker-colored ray florets than plants of 'Duebigon11'.

BRIEF DESCRIPTION OF THE PHOTOGRAPH

The accompanying photograph illustrates the overall appearance of the new *Bidens* plant showing the colors as true as it is reasonably possible to obtain in colored reproductions of this type. Colors in the photograph may differ slightly from the color values cited in the detailed botanical description which accurately describe the colors of the new *Bidens* plant.

The photograph comprises a side perspective view of a typical flowering plant of 'Duebigo14' grown in a container.

DETAILED BOTANICAL DESCRIPTION

The aforementioned photograph and following observations and measurements describe plants grown in 12-cm containers during the summer in a glass-covered greenhouse in Rheinberg, Germany and under cultural practices typical of commercial *Bidens* production. During the production of the plants, day and night temperatures averaged 18° C. and light levels averaged 4,500 lux. Plants were pinched one time three weeks after planting and were twelve weeks old when the photograph and description were taken. In the following description, color references are made to The Royal Horticultural Society Colour Chart, 2007 Edition, except where general terms of ordinary dictionary significance are used.

Botanical classification: *Bidens ferulifolia* 'Duebigo14'.

Parentage:

*Female parent*.—Proprietary selection of *Bidens ferulifolia* identified as code number B08-1708-002, not patented.

*Male parent*.—Proprietary selection of *Bidens ferulifolia* identified as code number F-020-003, not patented.

Propagation:

*Type*.—By vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; color, close to 155B.

*Rooting habit*.—Freely branching; moderately dense.

Plant description:

*Plant and growth habit*.—Compact, semi-upright to trailing and mounding plant habit; moderately vigorous growth habit.

*Branching habit*.—Freely branching habit with about eight primary lateral branches and numerous secondary lateral branches potentially forming at every node.

*Plant height*.—About 24 cm.

*Plant diameter or spread*.—About 50.5 cm.

*Lateral branches*.—Length: About 12.5 cm. Diameter: About 2.5 mm. Internode length: About 5.2 cm. Strength: Strong. Texture: Pubescent. Color: Close to 177A and 146C.

Leaf description:

*Arrangement*.—Opposite, simple.

*Length*.—About 2.7 cm.

*Width*.—About 2.2 cm.

*Shape*.—Roughly deltoid; pinnatisect.

*Apex*.—Apiculate.

*Base*.—Acute.

*Margin*.—Deeply incised; laciniate.

*Texture, upper and lower surfaces*.—Smooth, glabrous.

*Venation pattern*.—Pinnate.

*Color*.—Developing and fully expanded leaves, upper surface: Close to 141A; venation, close to 141A. Developing and fully expanded leaves, lower surface: Close to 141A; venation, close to 141B.

*Petioles*.—Length: About 6.3 mm. Diameter: About 1.5 mm. Texture, upper and lower surfaces: Smooth, glabrous. Color, upper and lower surfaces: Close to 146C.

Inflorescence description:

*Appearance*.—Single (daisy) inflorescence form with ray and disc florets forming acropetally on a receptacle; inflorescences positioned above and beyond the foliar plane on strong peduncles; inflorescences face upright to outwardly.

*Flowering habit*.—Freely flowering habit; about 50 to 70 inflorescences developing per plant.

*Fragrance*.—None detected.

*Natural flowering season*.—Plants flower continuously during the spring in Germany; early flowering habit, plants begin flowering about five weeks after planting.

*Inflorescence longevity*.—Individual inflorescences last about one week on the plant; inflorescences persistent.

*Inflorescence buds*.—Height: About 1 cm. Diameter: About 6 mm. Shape: Oblong. Color: Close to 9A.

*Inflorescence size*.—Diameter: About 4.5 cm. Depth (height): About 1.3 cm. Disc diameter: About 6.8 mm. Receptacle diameter: About 3.4 mm. Receptacle height: About 2.6 mm. Receptacle color: Close to 144A.

*Ray florets*.—Number of ray florets per inflorescence: About five to eight arranged in a single whorl. Length: About 1.8 cm to 2.1 cm. Width: About 1 cm. Shape: Elliptic to ovate. Apex: Emarginate. Base: Obtuse. Margin: Entire. Texture, upper and lower surfaces: Smooth, glabrous. Color: When opening, upper surface: Close to 14A. When opening, lower surface: Close to 12A. Fully opened, upper surface: Close to 14A; color becoming closer to 17A with development. Fully opened, lower surface: Close to 13A; color becoming closer to 17A with development.

*Disc florets*.—Number of disc florets per inflorescence: About 50. Shape: Tubular, elongated; apex, five-pointed. Length: About 8 mm. Diameter: About 1.5 mm. Color, when opening: Apex: Close to 163A. Mid-section: Close to 5A. Base: Close to 1C. Color, fully opened: Apex: Close to 14A. Mid-section: Close to 199A. Base: Close to 1B.

*Phyllaries*.—Quantity per inflorescence: About eight in a single whorl. Length: About 4 mm. Width: About 1.2 mm. Shape: Elliptical, elongated. Apex: Acute. Base: Truncate. Margin: Entire. Texture, upper and lower surfaces: Smooth, glabrous. Color, upper and lower surfaces: Close to 144A.

*Peduncles*.—Length, terminal peduncle: About 4.5 cm. Length, fourth peduncle: About 3.2 cm. Length, seventh peduncle: About 3 cm. Diameter: About 1.3 mm. Strength: Strong; flexible. Aspect: Upright to outwardly, inflorescences held above and beyond the foliar plane. Texture: Smooth, glabrous. Color: Close to 144A.

*Reproductive organs*.—Androecium: Present on disc florets only. Quantity per disc floret: Two. Filament length: About 2 mm. Filament color: Close to 7A.

Anther shape: Oval. Anther length: About 2.7 mm. Anther color: Close to 200C. Pollen amount: Scarce. Pollen color: Close to 7A. Gynoecium: Present on ray and disc florets. Pistil length: About 7 mm. Style length: About 4 mm. Style color: Close to 9C. Stigma shape: Bifurcate. Stigma color: Close to 15A. Ovary color: Close to 145A.

*Seeds*.—Quantity per inflorescence: About 40 to 50. Length: About 7 mm. Diameter: About 0.9 mm. Color: Close to 200A.

Disease & pest resistance: Plants of the new *Bidens* have not been shown to be resistant to pathogens and pests common to *Bidens* plants.

Garden performance: Plants of the new *Bidens* have exhibited good tolerance to rain and wind and have been observed to tolerate temperatures from about 5° C. to about 40° C.

It is claimed:

1. A new and distinct *Bidens* plant named 'Duebigo14' as illustrated and described.

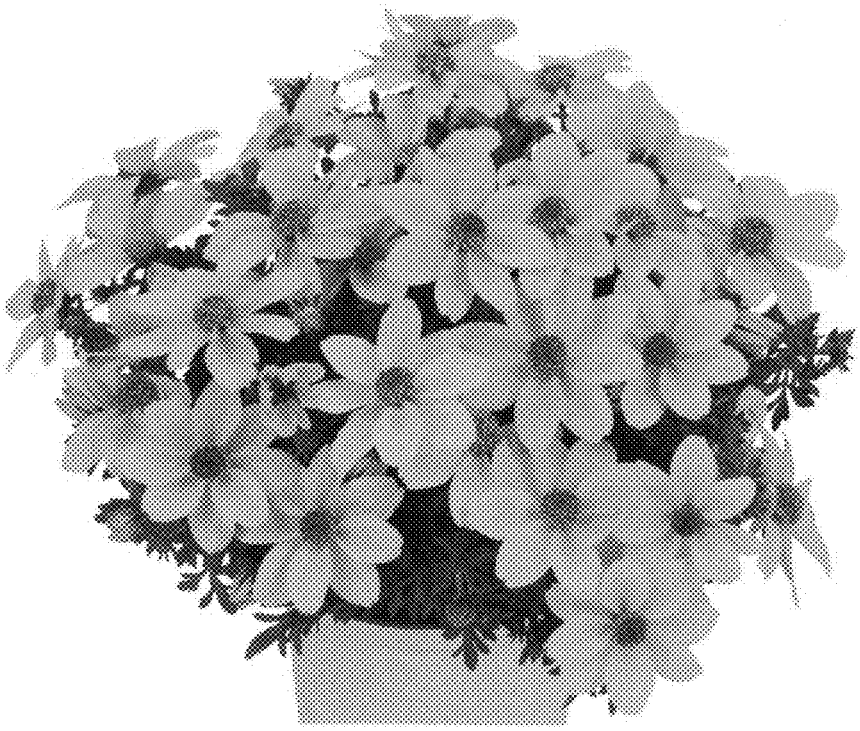

* * * * *